United States Patent

Arikka et al.

[11] Patent Number: 5,851,193
[45] Date of Patent: Dec. 22, 1998

[54] METHOD AND DEVICE FOR THE SIMULTANEOUS ANALYSIS OF AMBULATORILY RECORDED MOVEMENTS OF AN INDIVIDUAL'S DIFFERENT BODY PARTS

[76] Inventors: Harri Arikka, Haritunkatu 11 as 1, FIN-20740 Turku; Juha Markkula, Rykmentintie 64 J 131, FIN-20880 Turku; Hannu Lauerma, Karjakuja 41 as 4, FIN-20540 Turku, all of Finland

[21] Appl. No.: 776,930
[22] PCT Filed: Aug. 11, 1995
[86] PCT No.: PCT/FI95/00425
   § 371 Date: Feb. 11, 1997
   § 102(e) Date: Feb. 11, 1997
[87] PCT Pub. No.: WO96/04848
   PCT Pub. Date: Feb. 22, 1996

[30] Foreign Application Priority Data

Aug. 15, 1994 [FI] Finland ................................. 943741

[51] Int. Cl.⁶ ............................................ A61B 5/10
[52] U.S. Cl. ............................................ 600/595
[58] Field of Search ............................ 600/587, 595; 73/862, 862.042

[56] References Cited

U.S. PATENT DOCUMENTS

| | | | |
|---|---|---|---|
| 4,665,928 | 5/1987 | Linial et al. ...................... | 128/782 |
| 5,143,088 | 9/1992 | Marras et al. ...................... | 128/781 |
| 5,425,750 | 6/1995 | Mobey ............................... | 600/595 |

FOREIGN PATENT DOCUMENTS

| | | |
|---|---|---|
| 0 323 709 | 7/1989 | European Pat. Off. . |
| 0 535 508 | 4/1993 | European Pat. Off. . |

*Primary Examiner*—Max Hindenburg
*Attorney, Agent, or Firm*—Burns, Doane, Swecker & Mathis, L.L.P.

[57] ABSTRACT

A method and apparatus for the analysis of movements of several different parts of an individual's body recorded by ambulatory measurement involves registering the movements by an accelerometer attached to each body part to be monitored and storing the signals in memory. The signals registered by the different accelerometers are retrieved from the memory and conducted synchronously to a detector to thereby enable simultaneous monitoring of the movements of the different body parts. Signals based on movements of the limbs, head and/or the middle body and, if desired, signals based on other functions of the body like eye movements, breathing or pulsation of the heart are conducted synchronously to the detector to allow simultaneous monitoring of the movements of the various body parts and other functions of the body. The result is a precise qualitative and quantitative characterization of an individual's overall motor functions.

12 Claims, 2 Drawing Sheets

METHOD AND DEVICE FOR THE SIMULTANEOUS ANALYSIS OF AMBULATORILY RECORDED MOVEMENTS OF AN INDIVIDUAL'S DIFFERENT BODY PARTS

FIELD OF THE INVENTION

The invention relates to a method and apparatus for simultaneous monitoring of the movements of different parts of an individual's body and possibly the vital functions (breathing, pulse etc.) measured from the movements of body parts. The invention further relates to a method and apparatus for ambulatory registering and storing of the movement of a part of an individual's body.

BACKGROUND OF THE INVENTION

Ambulatory measurement of human movements has been carried out for several years in the fields of sleep research, behavioral science, epidemiology, and neurology (van Hilten J. J. et al., Electroencephalography and Clinical Neurophysiology 1993; 89:359–362).

The term "ambulatory" in this context denotes the fact that the movements are registered and stored with an individual which is not tied to the analyzer with any wires or any other means that would restrict free motion and activity. Therefore, registering and recording of movements are not spatially nor temporally bound to the analysis of them.

Ambulatory measurement of motion has been performed so that an accelerometer (also called an actometer in this field of application) has been attached to man's limb. A conventional single plane or uniaxial motion transducer has been used as the accelerometer, which registers the motion with varying sensitivity depending on the direction of the motion. Incorporated with the accelerometer is a digital memory into which a sample of the digitized and preprocessed accelerometer signal has been stored at intervals of 0.375–60 seconds, normally at intervals of 30 seconds. The data stored in the memory are then read out in a computer and the signal is directly plotted on paper or it is processed using some mathematical method (Reddihough D et al., Developmental Medicine and Child Neurology, 1990; 32:902–909).

Commercially available accelerometers have been used for validation e.g. in sleep research. Clinically, ambulatory accelerometers distinguish well sleep and wakefulness from each other both in adults and children (Sadeh A. et al., Journal of Ambulatory Monitoring 1989; Vol.2, No.3:209–216; Sadeh A et al., Pediatrics 1991; 87:494–499; Hauri P. J. & Wiseby J., Sleep 1992; 15(4):293–301). However, current actometric methods have provided contradictory results in sleep detection in adults with insomnia (Chambers M. J., Sleep 1994;17(5):405–408). Accelerometry has been utilized for characterization of the quality of limb movements in some neurological disorders like cerebral palsy, Huntington's disease, and Friedreich's ataxy (Reddihough D et al., Developmental Medicine and Child Neurology, 1991; 33:578–584).

The best place to attach an accelerometer to a human has been searched in some studies (van Hilten, 1993 and Webster J. B., et al., Med. & Biol. Eng. & Comp. 1982;20:741–744), but generally the investigation method has dictated the site of attachment of the accelerometer on the human body. The most popular way is to attach the accelerometer at the wrist of the non-dominant hand (van Hilten, 1993) and, in small children, one leg is used as the site of attachment (Sadeh, 1991). In one ataxy study the accelerometers were attached to the dominant hand and to the leg on the same side, yet the data the different accelerometers registered had been analyzed separately (Fillyaw M. J. et al., Journal of Neurological Sciences 1989;92:17–36).

Many of the limb movements have become lateralized i.e. they appear on one or the other side. In sleep a changeover phenomenon takes place in this lateralization: the movements of the non-dominant side become dominant (Lauerma H. et al., Biol. Psychiatry 1992; 32:191–194). The significance of the phenomenon is not known and it has not been investigated much. One study tried to describe the phenomenon by using accelerometers attached to each limb (Violani C. et al., J. Sleep Res. 1994; 3:suppl. 1:268). This study used a long measuring interval (60 seconds) for the accelerometers and, due to this large interval, characterization of the lateralization phenomenon provided somewhat contradictory results. It is also important to note in this connection that said study did not employ synchronized actometry of several limbs, in other words the question was not about multichannel actometry which partly explains the contradictory results.

Extended organized hand movements and small jerky limb movements of short duration have a different neural origin (Lauerma H. & Lehtinen I., J. Sleep Res. 1992; 1: suppl. 1: 130). The better the ability to distinguish limb movements from the inertial movements of the body and the various movements of a single limb the more complete is the characterization of nocturnal motor activity. For example, in some child neurological diseases, it is important to differentiate head movements from the movements of the body and the limbs during sleep (Thorpy M. J., Handbook of Sleep Disorders. New York. Marcel Dekker, 1990, 609–629). Limb movements are lateralized in normal people but in some disorders the lateralization phenomenon is abnormal (Lauerma et al., 1992).

It is therefore important for the progress of research that 1) one is able to register and store the movement of the part(s) of the body in question very accurately both quantitatively and qualitatively and that 2) one is able to differentiate the movement of specific part(s) of the body, e.g. movement of specific limb(s), from the movements of the body or other body parts and to monitor these movements simultaneously and in the same proportion.

However, prior art methods and equipment do not enable this kind of research. The prior art equipment used for ambulatory measurements have mainly employed uniaxial or single-plane accelerometers. For this reason, it has not been possible to record the movement accurately if the direction of the movement has deviated from the direction of the axes. In some studies (Webster 1982; Reddihough, 1990) three different accelerometers have indeed been used and the accelerometers were fitted close to the same place so that their axes were perpendicular to one another. However, each accelerometer signal was merely separately monitored. This arrangement is impractical because a combination of three accelerometers forms a large and heavy whole. In these experiments, there was no attempt to combine the signals of the various accelerometers to get an overall view of the movement.

U.S. Pat. No. 4,817,628 presents measurement of the movements of human facial muscles with an accelerometer comprising, in one embodiment, three orthogonal axes. The accelerometer is wired to the signal analyzer so that herein it is the question of a heavy laboratory equipment and not of an ambulatory registering device.

Another drawback with the contemporary instruments employed for ambulatory measurement of motion is the inadequate storing of the accelerometer signal. A digital memory has been used with a storing frequency of even as low as 1/min (Violani, 1994). Such a long storing interval does not give any information about the nature of the movements. These methods merely register movements with an acceleration above a certain threshold value according to the either-or principle. This limitation itself makes analysis of motion impossible.

The greatest drawback is that prior art devices do not enable a simultaneous analysis of the signals from accelerometers attached to various parts of the body. In those studies (e.g. Webster, 1982 and Fillyaw, 1989), wherein movements of different limbs have been simultaneously measured, there has been no attempt to monitor the movement simultaneously.

SUMMARY OF THE INVENTION

The objective of this invention is to remove the above drawbacks and obtain a new method and apparatus without the limitations described above.

The aim of the invention is to obtain a method and apparatus enabling simultaneous monitoring of signals registered and stored on basis of movements of different body parts in order to obtain an understanding of the qualitative and quantitative whole formed by individual's motor functions.

The second aim of the invention is to accomplish a more accurate ambulatory registering of the movements of a part or parts of an individual's body than has been possible with known solutions.

The above improvements can be applied alone and constitute as such a considerable step forward compared to the prior art technique. According to a recommended embodiment both improvements are combined. Combination of these improvements provides a new and particularly accurate and versatile method and apparatus for registering, storing and simultaneous monitoring of the movements of different body parts.

BRIEF DESCRIPTION OF THE DRAWING FIGURE

FIG. 1 is a graph of activity level versus time showing a four-limb actometric registering; and FIG. 2 is a schematic illustration of components forming the apparatus of the present invention

DETAILED DESCRIPTION OF THE INVENTION

The term "part of the body" denotes hereafter, when it is a question of a human body, limb, head or middle body. When it is a question of animals, this term also includes tail, ear etc.

The term "detector" denotes a device which illustrates visually like a visual display but it also includes devices illustrating by other means like e.g. devices illustrating by audiovisual means or combinations of them.

The term "individual" denotes man or animal.

Figure 2:
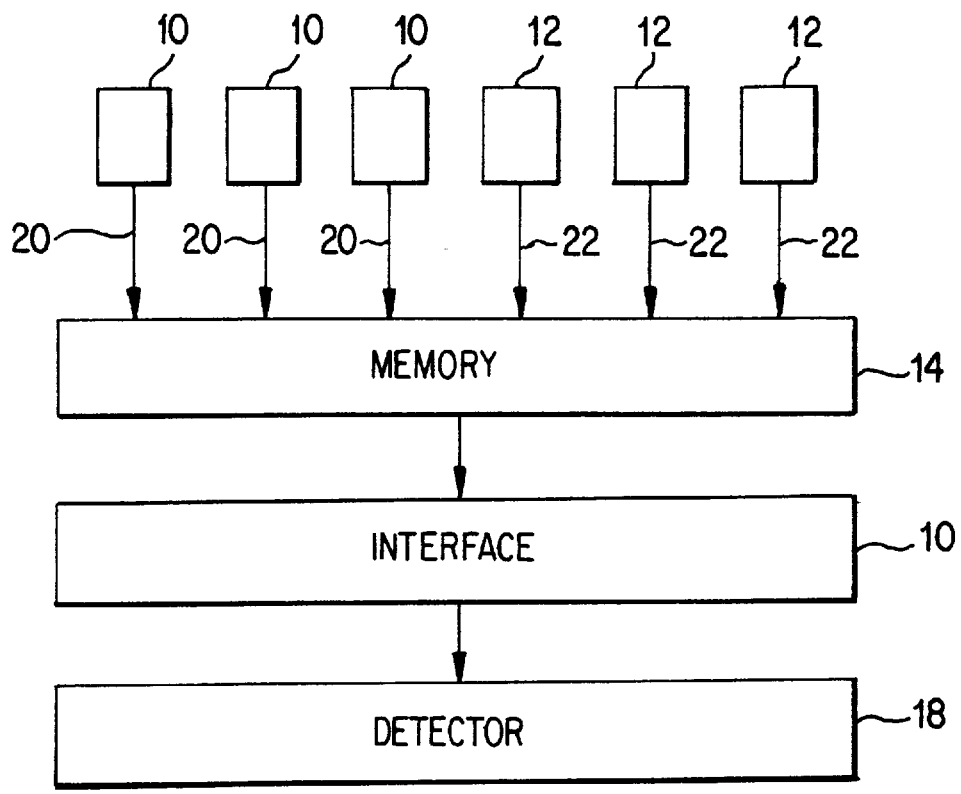

The invention therefore relates to a method and apparatus for the analysis of movements of several different parts of an individual's body recorded by ambulatory measurements, the apparatus comprising, as seen in FIG. 2 a detector 18 into which the signal registered and stored by the accelerometer 10 attached to each monitored body part is fed. According to the invention, the apparatus comprises several channels 10 for the signals registered by different accelerometers thereby allowing simultaneous monitoring of several body parts. According to one suitable embodiment of the invention, it additionally comprises separate channels 22 for signals based on other functions of the body like eye movements, breathing, or pulsation of the heart. In this way, movements of different limbs, head and/or the middle body and other functions of the body can be monitored simultaneously. Eye movements, pulsation of the heart and breathing also represent movements which can be measured with accelerometers 12 in the same way as movements of the body. Measurement of eye movement makes it possible to distinguish dozing/falling asleep of man from wakefulness. Furthermore, measurement of eye movement makes it possible to distinguish the REM stage, the important stage in sleep research, from other stages of sleep. Nowadays the REM stage is distinguished employing EOG-measurement based on electric potentials and this could be replaced with the new technique. In some applications it is possible to construct an alarm, which alarms if attentiveness is diminished, and incorporate it with the measurement of eye movements. A combination of measurements including measurement of truncal movements, eye movements, breathing movements and pulsation of heart constitutes such a comprehensive whole that it could partly replace the polygraphic registering (EEG, EKG, EOG, EMG) which has become a standard in sleep laboratories. The foremost advantage of the method is that the movements have been measured in an ambulatory manner.

According to one embodiment, the invention also relates to a method and apparatus for ambulatory registering and storing of the movements of a part of an individual's body. The essential components of the apparatus, which is attached to the body part, is an accelerometer 10 which registers the movement and transforms it into an electric signal corresponding to the force of the movement, and a memory 14 for storing the signal from the accelerometer. According to the invention, the accelerometer comprises three orthogonal axes. This kind of accelerometer registers the movements of the body part more accurately than the prior art accelerometer provided with one measuring plane or axis, which gives a correct representation of the movement only if the movement takes place along the axis. An accelerometer with three orthogonal axes accurately registers the strength of the movement even if the movement were not exactly along any of the axes but oblique with respect to each axis. When required, each axial signal can be separately stored into memory to be later, in a separate stage, combined into a sum signal. More preferably, the device to be attached to the body part also contains electronic components known per se whereby two or all three of the individual electric signals of the movement along the orthogonal axes of the movement can be combined into a sum signal. The accelerometer may be based on any material which transforms force into electric signal like piezoelectric or piezoresistive or the like material. To obtain a small and light device, it is appropriate to employ a capacitive accelerometer based on silicon wafers. The memory may be a digital memory known per se from ambulatory instruments. According to one recommended embodiment, the memory may be a digital memory with a high recording efficiency not previously used in ambulatory devices or a continuously recording analog memory which will be explained in greater detail in the following. The signal from each movement in the direction of the three orthogonal axes can be stored into the memory separately, one signal separately and two signals as the sum signal of two signals, or all three signals as the sum signal of the three signals.

The memory 18 purposed for storage of the accelerometer signal is preferably either an analog memory storing continuously or such a digital memory that has a sufficiently high storing frequency to be able to store accurately the signal of the movement i.e. at least 0.1 Hz but preferably over 50 Hz. The analog memory may be a magnetic tape or the like and the digital memory may be any digitally operating memory with a sufficiently high capacity. In choosing technical solutions, it should be noted that the device to be attached to the body part should be small and light. The accelerometer that registers the motion may be a standard uniaxial device but most preferably it has three orthogonal axes as explained above. If the accelerometer is of the latter type, it is recommended to equip the device to be attached to the body part with components which are capable of combining the individual electrical signals of the movement along one or two or all three orthogonal axes into a sum signal.

The memory need not be in the immediate proximity of the ambulatory registering apparatus. According to an alternative solution, in connection with the kinetic transducer is provided a preprocessor performing timing and other processing operations necessary for the communication at radio and other suitable frequencies. A transmitter fitted into a wristband transmits information about the results of measurements of the accelerometers either transmitting continuously in real time or as packed pulses (e.g. a period of one hour at a time). Thus the wristband or the like further accommodates a power supply and other equipment necessary for the transmitting and communication with the receiver. The signal is received e.g. by a receiver connected to a portable computer from which the information is directly conducted into the computer memory for storage.

The detector may be an analog device like an analog chart recorder but, according to a preferred solution, it is a computer display. The analyzer may be provided with components which form the sum signal from two or more signals. This enables e.g. the signal from the movement of one limb to be compared with the sum signal from the movements of other limbs. If the analyzer is provided with a processor, it is possible to program the processor to compute different numbers based on the signals and compare them with one another.

If the signal analyzer is a computer and the accelerometer signals have been stored in analog form, a means (so-called interface unit 16) is naturally needed before the computer, or a memory built inside the transducer which transforms the analog information into digital form. If so desired, it is also possible to incorporate with this interface unit components which form sum signals from individual signals.

The invention accomplishes a method and apparatus which is capable of registering and storing information very accurately in ambulatory circumstances. Thus stored signals based on movements can be analyzed simultaneously by means of the new multi-channel analyzer and thereby obtain quite new information because it is possible to distinguish movements of certain body parts from other truncal movements.

Figure 1:
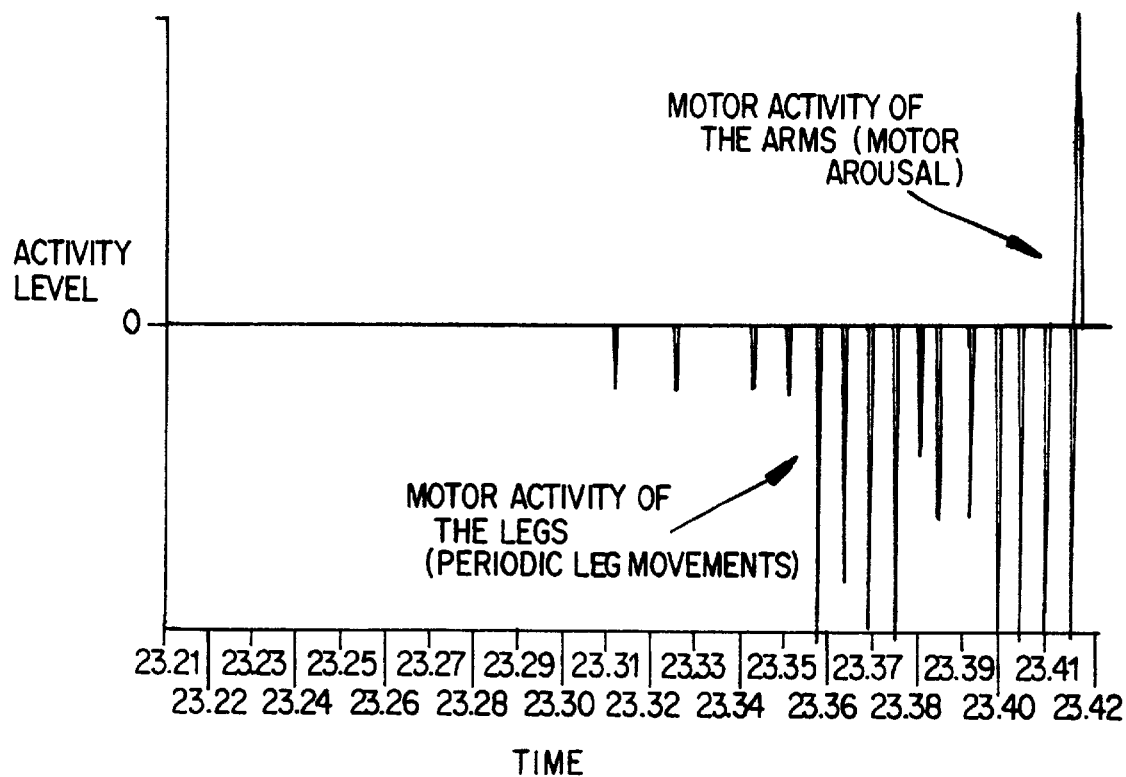

The enclosed FIG. 1 shows an example of a four-limb actometric registering during a 21 minute period of a subject suffering from a syndrome of periodic motor disorder and restless legs. Motor activity of legs is presented below the 0-line and activity of both arms is presented above the line. The figure demonstrates the advantages of a multichannel motor activity analysis compared to the conventional actometric methods. Besides the multichannel registering, a time window of 1.5 sec has been used which increases the resolution of the presentation compared to commonly used registering with a time window of about 30–60 sec. The result obtained with a conventional method would have been only one bar between 23.41 and 23.42. The information content of the multi-channel method can be further improved from this presentation by differentiating each limb and increasing the sampling frequency. However, as such the method enables detection of nocturnal periodic motor disorder from other motor activity while providing information on whether it will lead to change of posture or otherwise to motoric awakening. This has not been possible with prior art systems.

The described invention suits for both clinical use and research. Clinical applications already exist in the fields of sleep research and motoric research. In research this invention opens up new possibilities to gain new information in several fields. The invention opens up new possibilities in the characterization of diseases which manifest themselves as motoric disorders. For example, in psychiatry and neurology many diseases manifest as secondary motor disorders which may appear subclinically before the disease breaks out. Therefore, the invention may find use in diagnostics of various diseases. The inventions suits for mapping of the motions of both man and animals. Among the disciplines of research to mention are sleep research, motoric research, child neurology and psychiatry, sport medicine and training, physiatry and geriatrics, aviation medicine and diving medicine, military medicine, neuropsychology and cognition science, physiology and zoology, traffic and work safety, animal tests used in toxicity tests of medicaments and so on.

It is obvious to the specialist in the field that different embodiments of the invention may vary within the limits of the following claims.

We claim:

1. Method for analysis of movements of several different parts of an individual's body recorded by ambulatory measurement comprising registering the movements of several different parts of an individual's body by an accelerometer attached to each body part to be monitored, storing a signal from each accelerometer into memory, retrieving the signals registered by the accelerometers from the memory and synchronously conducting the signals retrieved from the memory to a detector thereby enabling simultaneous monitoring of the movements of the different body parts.

2. Method according to claim 1 wherein each accelerometer is an accelerometer comprising three orthogonal axes and including separately storing each signal from movements along the three orthogonal axes, or separately storing one signal and storing two signals as a sum signal of the two signals, or storing three signals as a sum signal of the three signals.

3. Method according to claim 2 including storing each signal either into an analog memory or into a digital memory whose storage frequency is at least 0.1 Hz, preferably over 50 Hz.

4. Method according to claim 1, wherein the movements of several different parts of the body include movements of limbs, head and/or middle body, and including registering eye movements, breathing, or heart pulsation, and synchronously conducting signals indicative of eye movements, breathing or heart pulsation to the detector.

5. Method according to claim 1, wherein the signals are conducted to an analog detector.

6. Method according to claim 1, wherein the signals are conducted to a computer.

7. Apparatus for analysis of movements of several different parts of an individual's body by ambulatory measurements, the apparatus comprising a plurality of accelerometers each adapted to be attached to a different part of a individual's body for producing a signal indicative of movements of the different parts of the individual's body, a detector into which the signals registered and stored by the accelerometer attached to each body part to be monitored is fed, and several channels for feeding the signals registered by different accelerometers to the detector to thereby allow simultaneous monitoring of several body parts.

8. Apparatus according to claim 7, including additional accelerometers for producing signals indicative of eye movements, breathing or heart pulsation and additional channels for feeding the signals from the additional accelerometers to the detector.

9. Apparatus according to claim 7, wherein the detector is an analog device.

10. Apparatus according to claim 7, wherein the detector is a computer.

11. Apparatus according to claim 7, including a memory for storing the signals from the accelerometers, said accelerometers each comprising three orthogonal axes and the memory being adapted to store each signal separately from three movements along the three orthogonal axes, or one signal separately and two signals as a sum signal of the two signals, or three signals as a sum signal of the three signals.

12. Apparatus according to claim 11, wherein the memory is either an analog memory or a digital memory whose storing frequency is at least 0.1 Hz, preferably over 50 Hz.

\* \* \* \* \*